United States Patent [19]
Barton
[11] 3,930,970
[45] Jan. 6, 1976

[54] PHOTOLYSIS OF ALCOHOL NITRITES

[75] Inventor: Derek Harold Richard Barton, London, England
[73] Assignee: Research Institute for Medicine and Chemistry Inc., Cambridge, Mass.

[22] Filed: Nov. 5, 1974
[21] Appl. No.: 521,098

[52] U.S. Cl. .............................................. 204/158 R
[51] Int. Cl.[2] .............................................. B01J 1/10
[58] Field of Search ................................ 204/158 R

[56] References Cited

UNITED STATES PATENTS 3,127,406 3/1964 Oliveto .............................. 204/158 R
3,154,569 10/1964 Ercoli et al. .................... 204/158 R

*Primary Examiner*—Howard S. Williams
*Attorney, Agent, or Firm*—Bacon & Thomas

[57] ABSTRACT

There is described the preparation of a mononitrate ester of a diol by photolysing in the presence of molecular oxygen a nitrite ester of an alcohol having a hydrogen atom conformationally adjacent to the hydroxy group and in which the atoms joining the hydrogen atom and the hydroxyl group include at least two adjacent atoms forming part of a ring.

15 Claims, No Drawings

PHOTOLYSIS OF ALCOHOL NITRITES

This invention relates to a novel process for the preparation of diol mononitrates and diols and ketoalcohols derived therefrom.

The photolysis of alcohol nitrites possessing a conformationally adjacent carbon-attached hydrogen atom, the "Barton reaction," is well known. A detail description of the reaction is to be found, for example, in U.S. Pat. No. 3,215,713. Under irradiation, the nitrite groups splits to yield a free NO group and an oxy radical. This latter radical captures the conformationally adjacent hydrogen atom to form a hydroxy group and a carbon radical and the NO migrates to this carbon radical to form a nitroso group. In modifications of this reaction, a halogen atom is introduced in place of the nitroso group to form a halohydrin which may, as in the case of steroids, be dehydrohalogenated to form a cyclic ether, and, from this a compound bearing a hydroxy group where the original hydrogen atom was may be prepared, the original hydroxy group having been replaced by hydrogen. Thus, for example, in the steroid field a 6-hydroxy compound yields a 6,19-oxido compound which may be reductively cleaved to the corresponding 19-hydroxy compound. This process is described in detail in, inter alia British Pat. Specification No. 1,106,296 and U.S. Pat. No. 3,354,150.

It has now been found, surprisingly, that in the presence of oxygen instead of a halogen free radical, the reaction proceeds in a different way, apparently with a radical transfer, resulting in the introduction of a nitrate ester (nitrooxy) group in place of the conformationally adjacent hydrogen atom and the restoration of the original hydroxy group. In this way a hydroxy group can be introduced while retaining an oxygen function in the original position.

According to the present invention therefore, there is provided a process for the preparation of a mononitrate ester of a diol whereby a nitrite ester of an alcohol having a hydrogen atom which is or is able to be conformationally adjacent to the hydroxy group and in which the atoms joining the hydrogen atom and the hydroxyl group include at least two adjacent atoms forming part of a ring is photolysed in the presence of molecular oxygen whereby a corresponding compound is formed in which the said hydrogen atom is replaced by a nitrooxy group.

The term 'conformationally adjacent' is used to mean that the atoms or groups concerned are so positioned that they may approach without appreciable molecular strain to within the distance normal for an interatomic bond. Thus, for example, in the steroids, the atoms attached to the $11\beta$ and 18 carbon atoms are more adjacent to each other than the $11\beta$ substituents are to the hydrogen atoms attached to carbon atoms at positions 8, 9, 12 or 13. Similarly, the substituents on the $11\beta$ are closer to the hydrogen atoms on the 19-carbon atom, than they are to the hydrogen atoms attached to the carbon atoms surrounding the 19-carbon position, that is to the hydrogen atoms attached to carbon atoms at positions 1, 5, 6, or 9.

In a similar manner, the atoms and groups linked to other carbon atoms in the steroid molecule, are conformationally adjacent to the hydrogen atoms linked to certain carbon atoms, of which the following are the principal examples: $1\beta$ group is conformationally adjacent to hydrogen attached to 11-carbon;

$2\beta$ group is conformationally adjacent to hydrogen attached to 19-carbon;

$4\beta$ group is conformationally adjacent to hydrogen attached to 19-carbon;

$6\beta$ group is conformationally adjacent to hydrogen attached to 19-carbon;

$7\alpha$ group is conformationally adjacent to hydrogen attached to 32-carbon;

$11\beta$ group is conformationally adjacent to hydrogen attached to 18- and 19-carbons;

$11\alpha$ group is conformationally adjacent to hydrogen attached to 1-carbon;

$15\alpha$ group is conformationally adjacent to hydrogen attached to 7-carbon;

18 group is conformationally adjacent to hydrogen attached to 11-carbon;

19 group is conformationally adjacent to hydrogen attached to 11-carbon, 2-carbon, 4-carbon and 6-carbon;

$20\alpha$ and $20\beta$ groups are conformationally adjacent to hydrogen attached to 18-carbon;

24 group is conformationally adjacent to hydrogen attached to 20-carbon.

It will be seen that in the above examples the conformationally adjacent atoms or groups are separated by a chain of four intervening carbon atoms, thereby allowing the conformationally adjacent atoms or groups to form part of a six-membered structure which, as is well-known, is normally substantially free from strain. Naturally, where the intervening carbon atoms form part of a structure in which bond rotation and movement is restricted, as in polycyclic structures such as steroids, the arrangement of all the bonds must allow the relevant atoms or groups to become adjacent. Other examples of compounds outside the steroid field in which the Barton reaction, and hence the present reaction, may be effected are given in detail in U.S. Pat. No. 3,215,713 and include, for instance, o-methylbenzyl nitrites, cyclooctyl nitrites, $\beta$-methyl-$\alpha$-naphthol nitrites and 2-methylpyrid-3-ylmethyl nitrites.

The reaction according to the present invention thus provides a simple route to an $\alpha,\delta$-diol mononitrate. Such a mononitrate may subsequently be reduced to free the diol itself as the end product, or alternatively, the free hydroxy group may be subjected to further reactions while the other hydroxy group is protected as the nitrate ester. In particular the free hydroxy group may be oxidised, for example with Jones' reagent (chromium trioxide/sulphuric acid) in acetone, to produce the corresponding hydroxyketone nitrate and, hence, the hydroxyketone.

Other reactions which may be effected while the nitrooxy group is present include, for example, dehydration to form an olefinic bond, isomerisation such as double bond shifts or epimerisation, esterification, etherification and hydrolysis of ester groups.

Under the reaction conditions employed for the photolysis, some $\delta$-hydroxyketone nitrate may also be formed, but this can be separated easily by conventional techniques such as chromatography. Where subsequent oxidation is required however no problem arises.

The photolysis is conveniently effected under conditions favouring a high oxygen concentration in the reaction medium. Thus a solvent which readily dissolves oxygen is desirable, e.g. aromatic compounds such as benzene, toluene and xylene; halogenated aromatic compounds such as hexafluorobenzene, chlorobenzene and the chlorotoluenes and chloroxylenes; halogenated hydrocarbons such as chloroalkanes, chlorofluoroalkanes, perfluoroalkanes and perfluoroalkylamines, in particular dichloroethane, methylene chloride, fluorotrichloromethane, chlorotrifluoromethane, dichlorodifluoromethane, 1,1,2-trichlorotrifluoroethane, and perfluorotributylamine; halogenated ethers, such as perfluoromethyltetrahydrofuran; and nitriles such as acetonitrile. Where the solvent dissolves oxygen well but does not sufficiently dissolve the nitrite ester, it is convenient to use another more powerful solvent in addition. Thus the nitrite may be dissolved in one solvent and a good oxygen solvent added thereto, either as a single phase mixture or as an emulsion of two phases.

The solubility of the oxygen is also improved by working at a low temperature, e.g. from 30° to 40° down to the freezing point of the reaction mixture.

The light used in the photolysis is preferably of a wavelength of 300 nm or more, advantageously of 300–380 nm.

In the general case it is not necessary for all the atoms intervening between the conformationally adjacent groups of the alcohol reactant to be carbon and in general it is possible for at least one intervening atom to be oxygen, nitrogen or sulphur, provided that the compound is chemically stable and that the atoms carrying the conformationally adjacent atoms or groups are both carbon. The process of the invention is thus of particular use in converting compounds having the grouping

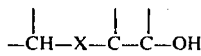

into diol mononitrates having the grouping

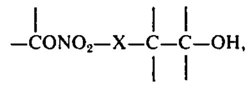

where X is a group

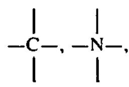

AS indicated above, the reaction is especially useful in steroid synthesis e.g. in the pregnane, lanostane, norpregnane, oestrane or cholestane series and particular applications are the preparation of 19-hydroxy steroids from 6-hydroxy steroids, the preparation of 18-hydroxy steroids from 11- and 20-hydroxy steroids, and the preparation of 32-hydroxy steroids from 7-hydroxy steroids.

By the term "steroids" we mean compounds having the basic cyclopentanoperhydrophenanthrene ring structure and which may contain various substituents and/or double bonds, e.g. a keto, hydroxy or acyloxy group in the 3-position; alkyl groups in any of 2-, 4-, 10-, 13-, 14- and 16-positions; a keto, ketal or ortho ester group at the 20-position; a keto group, or hydroxy and/or hydrocarbon or acyl (e.g. acetoxyacetyl) groups at the 17-position; a hydroxy or keto group at the 11- or 12-position, a hydroxy group at the 6-, 7- or 20-position, an esterified hydroxy group at the 21-position, a double bond at 5-position or the 1- and/or 4-position and a halogen atom such as fluorine or chlorine in the 11- or 6-position.

The nitrate product may, as described above, be reductively cleaved to yield the corresponding alcohol. The reducing agent may be any suitable for the purpose, in particular a metal/acid or metal/salt source of nascent hydrogen e.g. zinc and acetic acid or zinc and ammonium acetate.

The diol mononitrates prepared according to the present invention are precursors of alcohols having numerous uses, especially in the steroid field. Thus, for example, 19-hydroxy steroids are useful in the synthesis of 19-nor steroids. 18-Hydroxy steroids are useful intermediates in the synthesis of aldosterone derivatives and aldosterone antagonists. They are also reputed to be involved in hypertension.

$\Delta^1$-18-Hydroxy steroids, which may be produced by the process of the invention from $\Delta^2$-11-hydroxy steroids, are of value in the production of tritiumlabelled 18-hydroxy steroids such as 18-hydroxy corticosterone and 18-hydroxy-11-desoxy-corticosterone, which are of great use in metabolic and diagnostic studies. Particularly useful $\Delta^1$-18-hydroxy steroids are thus $\Delta^1$-18-hydroxy-corticosterone and $\Delta^1$-18-hydroxy-11-desoxycorticosterone.

The nitrite starting materials may conveniently be prepared by reaction of the corresponding alcohol with a nitrosyl halide, e.g. nitrosyl chloride, in a tertiary amine base such as pyridine or triethylamine.

While it is not wished to be bound by theoretical considerations, it is believed that under photolysis the conformationally adjacent carbon-attached hydrogenatom is captured by the carbon-attached oxygen atom of the nitrite group to yield a molecule of nitric oxide and a carbon free-radical which captures a molecule of oxygen and the molecule of nitric oxide to form a nitroperoxy group which rearranges instantaneously to form the stable nitrooxy group:

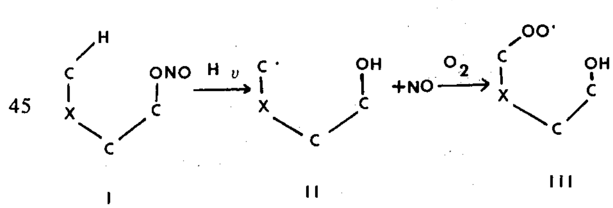

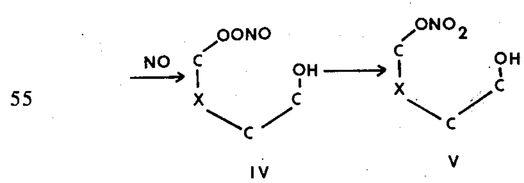

Since the reaction apparently procedes by way of reaction of the entity II with molecular oxygen, followed by NO. the radical II may also be generated by reaction of the free alcohol corresponding to the nitrite I with molecular oxygen together with a source of t-alkoxy radicals and NO most conveniently with a t-alkyl nitrite such as t-butyl nitrite. The t-alkoxy radical abstracts hydrogen from the OH group of the alcohol and the carbon-attached 0 radical so formed may then abstract the conformationally adjacent hydrogen atom to form the radical II.

The following examples illustrate the invention:

EXAMPLE 1

Irradiation of pregna-1,4-diene-11β-ol-3,20-dione,11-nitrite

The nitrite (700 mg) in dry acetonitrile was cooled to 5°–10°C and a stream of oxygen passed through the solution. After irradiation with a 200 Watt medium pressure lamp (Hanovia) for 25 mins. all the nitrite had been consumed. The solvent was removed under reduced pressure and the residue chromatographed (silica gel) to yield two major fractions, the larger of which was a mixture of the required product and the starting $\Delta^1$-11β-hydroxyprogesterone. Further chromatography and crystallization afforded 259 mg (34% yield) of 11,18-dihydroxy-pregna-1,4-diene-3,20-dione 18 nitrate. Crystallization from methanol/methylene chloride gave material with the following physical data: m.p. 162°–4°, $[\alpha]_D^{22}$ = +159° (C = 0.9 $CHCl_3$), IR: $\nu_{max.}^{KBr}$ 3450(*m*), 1700(*m*), 1650(*s*), 1620(*s*), 1610(*s*), 1270(*s*) $cm^{-1}$, UV: $\lambda_{max.}^{MeOH}$ 243 mμ (ε 14,900),

| NMR ($CDCl_3$): protons assigned | At δ values |
|---|---|
| $C_1$ | 7.2 (*d*, J=10 Hz) |
| $C_2$ | 6.2 (*dd*,J=10 and 2 Hz) |
| $C_4$ | 5.95 (broad *s*) |
| $C_{18}$ | 4.55 (*q*, $J_{AB}$=10 Hz) |
| $C_{11}$ | 4.4 (*m*) |
| $C_{21}$-methyl | 2.1 (*s*) |
| $C_{19}$-methyl | 1.35 (*s*) |

Analysis $C_{21}H_{37}NO_6$: Requires C, 64.76%; H, 6.99%; N, 3.60%; Found 64.90; 6.95; 3.46;

Mass spec. $M^+$ not seen, base peak at M-63

EXAMPLE 2

Preparation of pregna-1,4-diene-18-ol-3,11,20-trione 18-nitrate

The product from the above reaction (100 mg) was taken up in acetone (10 mls), and treated with Jones' reagent (0.2 mls). After stirring for 10 mins. at room temperature the reaction mixture was poured into sodium bicarbonate solution and extracted with ethyl acetate. The extracts were washed with water, dried ($Na_2SO_4$) and evaporated to dryness under reduced pressure. The residue was chromatographed (silica-gel) to give the required product (89 mg. 89%). Crystallization from ethyl acetate/hexane gave material with the following physical data: m.p. 146°–7°, $[\alpha]_D^{24}$ = +205° (C = 0.8 $CHCl_3$), IR $\nu_{max.}^{KBr}$ : 1705(*s*), 1660(*s*), 1630(*s*), 1605(*m*), 1275(s) $cm^{-1}$, UV $\lambda_{max.}^{MeOH}$ : 240 mμ (ε = 16,000),

| NMR ($CDCl_3$): Protons assigned | at δ values |
|---|---|
| $C_1$ | 7.73 (*d*, J=10 Hz) |
| $C_2$ | 6.20 (*dd*, J=10 and 2 Hz) |
| $C_4$ | 6.10 (broad *s*) |
| $C_{18}$ | 4.40 (*q*, $J_{AB}$=11 Hz) |
| $C_{21}$-methyl | 2.17 (*s*) |
| $C_{19}$-methyl | 1.45 (*s*) |

Analysis: $C_{21}H_{25}N_1O_6$: Requires C, 65.10%; H, 6.50%; N, 3.62%; Found 64.96; 6.46; 3.42;

Mass spec. $M^+$ 387 (very faint), base peak (M-63).

EXAMPLE 3

Preparation of pregna-1,4-diene-18-ol-3,11,20-trione

The product of the above reaction (100 mg) was taken up in 10 mls of 90% aq. acetic acid and treated with zinc dust (500 mg). The mixture was stirred at room temperature for 10 mins. then poured into sodium bicarbonate solution and extracted with ethyl acetate. The extracts were washed well with water, dried ($Na_2SO_4$) and the solvent removed under reduced pressure. The residue was crystallized from methylene chloride/methanol to give material with the following physical data: m.p. 185°–197°, IR: $\nu_{max.}^{KBr}$ 3450 (*m*), 1700(*m*), 1660(*s*), 1620(*m*), 1605(*w*) $cm^{-1}$.

| NMR ($CDCl_3$): Protons assigned | at δ values |
|---|---|
| $C_1$ | 7.55 (*d*. J=10 Hz) |
| $C_2$ | 6.17 (*dd* J=10 and 2 Hz) |
| $C_4$ | 6.08 (broad *s*) |
| $C_{18}$ | 3.51 (*q* $J_{AB}$=9 Hz) |
| also | 3.47 (*q* $J_{AB}$=7 Hz) |
| $C_{21}$-methyl | 1.40 (*s*) |
| $C_{19}$-methyl | 1.37 (*s*) |

Analysis: $C_{21}H_{26}O_4$ *Requires*: *c*, 73.65%; H, 7.65%; Found: C, 73.39; H, 7.72;

EXAMPLE 4

Preparation and irradiation of pregn-5-ene-3β,20β-diol, 3-acetate 20 nitrite a. The 20β-alcohol (2.5 g) was taken up in dry pyridine (40 m/s), cooled to 0°–5°C and treated with nitrosyl chloride until a permanent brown colour was observed. The mixture was stirred for a further 10 min. then poured into ice-water. The product was filtered off, washed with water, taken up in ethyl acetate, washed with water, dried ($Na_2SO_4$) and evaporated to dryness. Yield 2.4 g (91%).

Crystallization from methylene chloride/ethanol at room temperature afforded colourless plates. m.p. 153°–154.5° (dec.). IR: $\nu_{max.}^{KBr}$ 1735(*s*), 1635(*s*), 1600(*m*), 1250(*s*), 780(*s*) $cm^{-1}$. $[\alpha]_D^{21}$ = 87° (*c* = 1.05 $CHCl_3$).

| NMR ($CDCl_3$): Protons assigned | at δ values |
|---|---|
| $C_{20}$ | 5.4 (*m*, broad) } over- |
| $C_6$ | 5.3 (*m*) } lapping |
| $C_3$ | 4.6 (*m*, very broad) |
| O-acetyl | 2.0 (*s*) |
| $C_{21}$-methyl | 1.33 (*d*, J 6 Hz) |
| $C_{19}$-methyl | 0.98 (*s*) |
| $C_{18}$-methyl | 0.66 (*s*) |

b. The 20β-nitrite (2.0 g) was taken up in dry acetonitrile (500 mls) and oxygen passed through the solution cooled to −20°C. Irradiation was carried out at this temperature for 1 hr. — all nitrite being consumed. The solvent was removed under reduced pressure and the residue chromatographed over silica using benzene containing 0% rising to 5% ethyl acetate. This resulted in four major components which were further chromatographed (silica gel, prep. t.l.c.) to give:

1. 505 mg (27%) of pregnenolone acetate VII 2. 400 mg (22%) of the starting 20β-alcohol VIII
3. 295 mg of the required 20β-alcohol-18-nitrate IX (14%) yield
4. 160 mg of the 20-keto-18-nitrate X (8% yield)

Fraction 3 — the required product was crystallized from hexane to give very light needles. m.p. 140°–1°. IR: $\nu_{max.}^{KBr}$ 3650(*w*), 1725(*s*), 1620(*s*), 1280(*m*), 1240(*s*) $cm^{-1}$. $[\alpha]_D^{21}$ = −51° (c=0.9 $CHCl_3$).

| NMR: ($CDCl_3$) | Protons assigned | at δ values |
|---|---|---|
| | $C_6$ | 5.35 (*m*) |
| | $C_3$ | 4.6 (*m*, very broad) |
| | $C_{18}$ | 4.50 (*q*. $J_{AB}$=10 Hz) |
| | $C_{20}$ | 3.7 (*m*, broad) |
| | O-acetyl | 2.00 (*s*) |
| | $C_{21}$-methyl | 1.15 (*d*, J=6 Hz) |
| | $C_{19}$-methyl | 1.03 (*s*) |

Analysis: $C_{23}H_{35}N_1O_6$ Requires: C=65.53; H=8.37; N=3.32%; C, 65.60; H, 8.30; N, 3.29%;

Mass spectrum $M^+$ not seen, base peak at M-60, (M-123).

Fraction 4 was identical in all physical data to the keto-nitrate obtained by oxidation of fraction 3 as follows.

EXAMPLE 5

Preparation of pregn-5-ene-3β,18-diol-20-one, 3-acetate 18 nitrate

The 20β-hydroxy-18-nitrate from Fraction 3 of Example 4 (75 mg) was taken up in acetate (5 mls), and treated with Jones' reagent (0.1 ml). After stirring for 2 mins. the reaction mixture was poured into water, the product extracted into methylene chloride, washed with sodium bicarbonate solution, water and dried ($Na_2SO_4$). After removal of the solvent the residue (68 mg,91%) was found to be essentially pure by t.l.c. and was recrystallized from hexane to give colourless plates. m.p. 156°–7°. IR: $\nu_{max.}^{KBr}$ 1725(*s*), 1705(*s*), 1635(*s*), 1275(*s*), 1240(*s*) $cm^{-1}$. $[\alpha]_D^{21}$ = +24° (c=0.95, $CHCl_3$).

| NMR ($CDCl_3$): | Protons assigned | at δvalues |
|---|---|---|
| | $C_6$ | 5.35 (*m*) |
| | $C_3$ | 4.5 (*m*, very broad) |
| | $C_{18}$ | 4.34 (broadened singlet) |
| | $C_{21}$-methyl | 2.25 (*s*) |
| | O-acetyl | 2.00 (*s*) |
| | $C_{19}$-methyl | 1.03 (*s*) |

Analysis: $C_{23}H_{33}N_1O_6$ Requires: C=65.84% H=7.93% N=3.34% Found: C, 65.92; H, 7.94; N, 3.25;

Mass spectrum $M^+$ not seen, base peak at M-60 (M-123).

EXAMPLE 6

Preparation and irradiation of pregn-5-ene-3β-20α-diol, 3-acetate 20 nitrite a. The procedure used was identical to that employed for the 20β-nitrite preparation in Example 4. 1.1 g of the 20α-alcohol afforded 1.08 g (91%) of the nitrite. Crystallization from methylene chloride/methanol afforded colourless needles. m.p. 110°–111°. IR: $\nu_{max.}^{KBr}$ 1735(*s*), 1630(*s*), 1245(*s*), 800(*s*) $cm^{-1}$. $[\alpha]_D^{21}$ = −31° (c=0.8 $CHCl_3$).

| NMR ($CDCl_3$): | Protons assigned | at δ values |
|---|---|---|
| | $C_{20}$ | 5.5 (*m*, broad) |
| | $C_6$ | 5.4 (*m*) |
| | $C_3$ | 4.6 (*m*, very broad) |
| | O-acetyl | 2.00 (*s*) |
| | $C_{21}$-methyl | 1.45 (*d* J=6 Hz) |
| | $C_{19}$-methyl | 1.03 (*s*) |
| | $C_{18}$-methyl | 0.80 (*s*) |

b. The same irradiation procedure as in Example 4 was used. 1.0 g of the nitrite in acetonitrile (500 mls) was irradiated at 0° to −20°C in the presence of oxygen for 35 mins. Chromatography then gave 506 mg (47% yield) of the required nitrate. $[\alpha]_D$ = −44°.

Analysis: $C_{23}H_{35}N_1O_6$ Requires: C=65.53; H=8.37; N=3.32%; Found: C, 65.74; H, 8.34; N, 3.20;

EXAMPLE 7

Preparation of pregn-5-ene-3β,18-diol-20-one, 3-acetate, 18-nitrate

The 20α-hydroxy-18-nitrate from Example 6 (100 mg) was oxidized with Jones' reagent (0.15 mls) in acetone (10 mls) in the same way as the 20β-hydroxy compound in Example 5 to give the 20-keto-18-nitrate (89 mg,89%). All physical data were identical with that reported in Example 5.

EXAMPLE 8

Preparation and irradiation of 1-dehydrocorticosterone-21-acetate, 11-nitrite a. 1-Dehydrocorticosterone acetate (2.4 g) in pyridine (20 mls) was cooled in an ice-bath and treated with nitrosyl chloride until a brown colouration persisted. The mixture was stirred for a further 10 mins. then poured into cold water and the product filtered off and washed well with water. This solid was dissolved in methylene chloride, washed with water, dried ($Na_2SO_4$) and evaporated to dryness. Yield 2.5 g (96%). An analytical sample was crystallized from ethyl acetate/hexane. m.p. 165°–7° (dec.). IR: $\nu_{max.}^{KBr}$ 1755(*s*), 1720(*s*), 1660(*s*), 1625(*m*), 1610(*w*), 1240(*s*) $cm^{-1}$. UV: $\lambda_{max.}^{MeOH}$ 241 mμ (ε 16,600). $[\alpha]_D^{20}$ = +218° (c=0.98 $CHCl_3$).

| NMR ($CDCl_3$)'': | Protons assigned | at δ values |
|---|---|---|
| | $C_1$ | 6.88 (*d*, J=10 Hz) |
| | $C_2$ | 6.23 (*dd*, J=10 and 2 Hz) |
| | $C_4$ | 5.98 (broad *s*) |
| | $C_{11}$ | 6.1 (*m*) |
| | $C_{21}$ | 4.55 (*s*) |
| | O-acetyl | 2.12 (*s*) |
| | $C_{19}$-methyl | 1.20 (*s*) |
| | $C_{18}$-methyl | 0.80 (*s*) |

b. The nitrite in acetonitrile (550 mls) containing triethylamine (0.5 mls) was irradiated as described above for 70 mins. at 0°C in the presence of oxygen. The solvent was removed under reduced pressure and the residue chromatographed to give the required 18-nitrite (325 mg, 32%) containing some 5% of an impurity. m.p. 102°–12°, $[\alpha]_D$ = +162°.

Calculated for: $C_{23}H_{29}N\ O_8$: Requires C, 61.73; H, 6.53; N, 3.13; Found: C, 61.64; H, 6.50; N, 2.90.

EXAMPLE 9

Preparation of 18-Hydroxy Pregnenolone Acetate

A solution of the 18-nitrate of pregnenolone acetate obtained in Examples 5 and 7 (100 mg) in methanol (20 mls) was cooled to 0°C and ammonium acetate (1.0 g) added, followed by zinc dust (1.5 g). The reaction mixture was stirred at 0°–5°C for 90 mins., before being diluted with water and methylene chloride. The insoluble material was filtered off, the organic phase separated and the aqueous phase extracted twice methylene chloride. The combined methylene chloride extracts were washed with water, dried ($Na_2SO_4$) and evaporated to dryness (97 mg). Crystallization from acetone gave 69 mg (78%) of material having m.p. 169°–171°; successive crystallizations from acetone eventually raised the m.p. to 171°–3° (lit. m.p. 171°–4°)* $[\alpha]_D^{25} = -2°$ (c=0.6, $CHCl_3$) (lit. $[\alpha]_D$ +6°)*. IR: $\nu_{max.}^{KBr}$ 3500(*m*), 1735(*s*), 1240(*s*) $cm^{-1}$.

*Sykes and Kelley, J. Chem. Soc. C. 1968, 2913.

| NMR ($CDCl_3$): | Protons assigned | at δ values |
|---|---|---|
| | $C_6$ | 5.3 (*m*) |
| | $C_3$ | 4.5 (*m*, very broad) |
| | $C_{18}$ | 4.68 (broadened *s*) |
| | O-acetyl | 2.00 (*s*) |
| | $C_{21}$-methyl | 1.46 (*s*) |
| | $C_{19}$-methyl | 0.94 (*s*) |

Analysis: $C_{23}H_{34}O_4$: Requires: C=73.76; H=9.15; Found: C=73.86; H=8.94;

Mass spectrum: weak molecular ion at 374, (M-18), (M-46), (M-60), (M-78), (M-90), (M-93).

EXAMPLE 10

Preparation of 18-nitrooxy progesterone

A solution of the 18-nitrooxy-pregnenolone acetate from Examples 5 and 7 (395 mg) in methanol (15 mls) was treated with perchloric acid (0.5 mls). After 6 hrs. at room temperature a further 0.25 mls of perchloric acid were added and the stirring continued for 2 hrs.; t.l.c. then showed essentially complete reaction. Diluted with water to give a semi-solid product, 18-nitrooxy-pregnenolone, which was taken up in methylene chloride, washed with water, dried ($Na_2SO_4$) and evaporated to dryness (312 mg).

| NMR: ($CDCl_3$) | Protons assigned | at δ values |
|---|---|---|
| | $C_6$ | 5.25 (*m*) |
| | $C_{18}$ | 4.30 (AB, *q*, J=11 Hz) |
| | $C_3$ | 3.5 (*m*, very broad) |
| | $C_{21}$-methyl | 2.20 (*s*) |
| | $C_{19}$-methyl | 0.97 (*s*) |

Attempts to crystallize this material were unsuccessful, therefore it was carried through without further purification.

The above product (300 mg) in dry toluene (35 mls) containing 1-methyl-4-piperidone (3 mls) was refluxed under nitrogen using a Dean-Stark apparatus. The first 5 mls. of distillate were discarded and then a solution of aluminium isopropoxide (490 mg) in dry toluene (2 mls) was added dropwise over a few minutes. The mixture was refluxed for a further 6 hours, cooled, washed 3 times with 1% $H_2SO_4$, with water and then dried ($Na_2SO_4$) and evaporated to dryness. Preparative t.l.c. (silica gel) afforded the required 18-nitrooxy-progesterone, 126 mg, 47% yield. Crystallization from ethyl acetate/hexane afforded material with the following physical data: m.p. 145°–6°. IR $\nu_{max.}^{KBr}$ 1700(*m*), 1665(*s*), 1620(*s*) 1280(*s*) $cm^{-1}$. UV $\lambda_{max.}^{MeOH}$ 239–40 mμ (ε = 17,200). $[\alpha]_D^{25} = +190°$ (c=0.87 $CHCl_3$).

| NMR ($CDCl_3$): | Protons assigned | at δ values |
|---|---|---|
| | $C_4$ | 5.69 (*s*, broadened) |
| | $C_{18}$ | 4.35 (AB, *q*, J=11 Hz) |
| | $C_{21}$-methyl | 2.17 (*s*) |
| | $C_{19}$-methyl | 1.20 (*s*) |

Analysis: $C_{21}H_{29}N_1O_5$ Requires: C, 67.17; H, 7.78; N, 3.73%; Found: C, 67.14; H, 7.61; N, 3.53;

Mass spectrum: Molecular ion at 375, (M-28), (M-63, base peak).

When a Jones oxidation was attempted instead of the above Oppenauer oxidation, the major product isolated had the following physical data, in accord with 6-keto-18-nitrooxy-progesterone, m.p. 178°–189° (gas evolution). IR $\nu_{max.}^{KBr}$: 1700(*s*), 1685(*s*), 1630(*s*), 1275(*s*), 870(*s*,broad) $cm^{-1}$.

UV $\lambda_{max.}^{MeOH}$: 250 mμ (ε = 11,600). $[\alpha]_D^{28.7} = +45°$ (c=0.51 $CHCl_3$).

| NMR ($CDCl_3$): | Protons assigned | at δ values |
|---|---|---|
| | $C_4$ | 6.10 (*s*) |
| | $C_{18}$ | 4.36 (*s*) |
| | $C_{21}$-methyl | 2.20 (*s*) |
| | $C_{19}$-methyl | 1.16 (*s*) |

Analysis: $C_{21}H_{27}N_1O_6$ requires: C, 64.76%; H, 6.99; N, 3.60. Found: C, 64.77%; H, 6.99; N, 3.72.

Mass spectrum: very weak molecular ion at 389 mμ, (M-46), (M-63), (M-75), (M-77) mμ.

EXAMPLE 11

Preparation of 18-hydroxyprogesterone

Using the same procedure as that described in Example 9 for the preparation of 18-hydroxypregnenolone acetate, 50 mg of 18-nitrooxy-progesterone afforded 51 mg of crude product. Chromatography on silica gel (prep. t.l.c.) eluting with 5% acetone/$CH_2Cl_2$ gave 31 mg (71%) of 18-hydroxyprogesterone which was recrystallized from aqueous acetone to give material with the following physical data: m.p. 159°–161° mainly but some crystals remained in the melt up to 163. IR: $\nu_{max.}^{KBr}$ 3500(*m*), 1660(*s*), 1620(*w*) $cm^{-1}$. UV $\lambda_{max.}^{MeOH}$: 240 mμ (ε = 16,900). $[\alpha]_D^{22.5}$: +124° (c=0.79, $CH_2Cl_2$).

| NMR ($CDCl_3$): | Protons assigned | at δ values |
|---|---|---|
| | $C_4$ | 5.66 (*s*, broadened) |
| | $C_{18}$ | 3.66 (*s*, broadened) |
| | $C_{21}$-methyl | 1.43 (*s*) |
| | $C_{19}$-methyl | 1.08 (*s*) |

Analysis $C_{21}H_{30}O_3$ Requires: C, 76.33; H, 9.15; Found: C, 76.65; H, 9.03.

Mass spectrum: Molecular ion at 330 is very weak, (M-18), (M-60), (M-103).

EXAMPLE 12

Irradiation of $\Delta^1$-corticosterone 21-acetate, 11-nitrite in the presence of oxygen A solution of the nitrite (2.4 g) in dry acetonitrile (550 mls) containing triethylamine (0.5 mls) was irradiated at 0°–10° for 70 mins. under oxygen using a 200 Watt medium pressure mercury lamp. The solvent was removed under reduced pressure and the residue chromatographed (silica gel prep. t.l.c.) to afford 18-nitrooxy-$\Delta^1$-corticosterone 21-acetate (875 mg, 34%) which was rectystallized from ethyl acetate/hexane, yielding colourless needles, m.p. 110°–115° softening from 106° but some crystals remaining in the melt until 118°. Sealed tube m.p. 113°–115°, softening from 106°, gas evolution. $[\alpha]_D^{21}$ = +162 (c = 0.4, $CHCl_3$). UV $\lambda_{max.}^{MeOH}$: 240 mμ (ε = 15,800). IR $\nu_{max.}^{KBr}$: 3550(*m*, broad), 1755(*m*), 1730(*m*), 1660(*s*), 1630(*s*), 1280(*s*) $cm^{-1}$.

| NMR($CDCl_3$): | Protons assigned | at δ values |
|---|---|---|
| | $C_1$ | 8.23 (*d*, J=10 Hz) |
| | $C_2$ | 6.20 (*d.d.*, J=10 and 2 Hz) |
| | $C_4$ | 5.97 (broad, *s*) |
| | $C_{11}$ | |
| | $C_{18}$ | All overlapping at 4.2–5 |
| | $C_{21}$ | |
| | O-acetyl | 2.10 (*s*) |
| | $C_{19}$-methyl | 1.43 (*s*) |

Analysis: $C_{23}H_{29}N_1O_8$ Requires: C, 61.73%; H, 6.53; N, 3.13; Found C, 61.64%; H, 6.50; N, 2.90.

EXAMPLE 13

Oxidation of 18-nitrooxy-$\Delta^1$-corticosterone 21-acetate

The above 18-nitrate (250 mg) in acetone (30 mls) was treated with 0.3 mls. Jones' reagent. After stirring at room temperature for 5 minutes the reaction mixture was diluted with water and the product extracted into ethyl acetate, washed with sodium bicarbonate solution and with water, dried ($Na_2SO_4$) and evaporated to dryness. Chromatography of the residue (prep. t.l.c., silica gel) gave 18-nitrooxy-$\Delta^1$-dehydrocorticosterone 21-acetate (219 mg, 88%). Crystallization from isopropanol gave material with the following physical data: m.p. 130°–2°. $[\alpha]_D^{20}$ = +298° (c = 0.5, $CHCl_3$). IR $\nu_{max.}^{KBr}$: 1760(*s*), 1730(*s*), 1710(*s*), 1660(*s*, broad), 1615(*s*), 1290(*s*), 1220(*s*) $cm^{-1}$. UV $\lambda_{max.}^{MeOH}$: 239 mμ (ε = 16,200).

| NMR ($CDCl_3$): | Protons assigned | at δ values |
|---|---|---|
| | $C_1$ | 7.70 (*d*, J=10 Hz) |
| | $C_2$ | 6.14 (*d.d.*, J=10 and 2 Hz) |
| | $C_4$ | 6.05 (broad, *s*) |
| | $C_{21}$ | 4.60 (*s*) |
| | $C_{18}$ | 4.38 (AB, *q*, J=11 Hz) |
| | O-acetyl | 2.13 (*s*) |
| | $C_{19}$-methyl | 1.42 (*s*) |

Analysis: $C_{23}H_{27}N_1O_8$ Requires: C=62.01; H=6.11; N=3.14; Found C=62.19; H=6.13; N=3.16;

Mass spectrum: Molecular ion at 445 (weak), (M-46), (M-61), (M-63).

EXAMPLE 14

Preparation and irradiation of pregna-1,4-dien-20β-ol-3-one 20-nitrite a. A solution of pregna-1,4-dien-20β-ol-3-one (110 mg) in pyridine (4 mls) was cooled in an ice-bath then treated with nitrosyl chloride until a permanent brown colouration was observed. The mixture was stirred for a further 5 minutes and then poured into water. The solid product was filtered off, washed with water, taken up in methylene chloride, washed again with water, dried ($Na_2SO_4$) and evaporated to dryness (112 mg, 93%). Crystallization was carried out at below 40°C from ethyl acetate/hexane with a trace of pyridine to afford the nitrite, m.p. 145°–7°. IR $\nu_{max.}^{KBr}$: 1665(*s*), 1600(*w*), 880(*s*) $cm^{-1}$. $[\alpha]_D^{26}$ = +52° (c = 0.51, $CH_2Cl_3$). UV $\lambda_{max.}^{MeOH}$: 244 mμ (ε = 17,200).

| NMR ($CDCl_3$): | Protons assigned | at δ values |
|---|---|---|
| | $C_1$ | 6.90 (*d*, J=10 Hz) |
| | $C_2$ | 6.10 (*d,d*, J=10 and 2 Hz) |
| | $C_4$ | 6.00 (broad, *s*) |
| | $C_{20}$ | 5.35 (*m*) |
| | $C_{21}$-methyl | 1.33 (*d*, J=6 Hz) |
| | $C_{19}$-methyl | 1.21 (*s*) |
| | $C_{18}$-methyl | 0.73 (*s*) |

b. The 20β-nitrite (XII) (8.05 g) was irradiated in 4 g batches, each in dry chlorobenzene (500 mls) containing triethylamine (0.5 mls), under the usual conditions in the presence of oxygen about 150 mins. being required for complete consumption of the nitrite. The solvent was evaporated off under reduced pressure and the residue taken up in acetone (100 mls) and cooled in an ice-bath. Jones' reagent (15 mls) was added dropwise over 5 minutes, the mixture was stirred for a further 10 minutes, and then diluted with water (300 mls). The product was extracted into ethyl acetate, washed with sodium bicarbonate and with water, dried and evaporated to dryness. Two 1 gram aliquots were then treated as follows:

A. Preparative t.l.c. (silica gel) and crystallization from ethyl acetate/hexane afforded a total of 380 mg (33%) of 18-nitrooxypregna-1,4-diene-3,20-dione having the following physical data: m.p. 148.5°–150° (dec-.—gas evolution). $[\alpha]_D^{24.5}$=+128 (c=1.7, $CH_2Cl_2$). IR $\nu_{max.}^{KBr}$: 1700(*m*), 1660(*s*), 1635(*s*), 1620(*m*, shoulder), 1600(*w*), 1275(*s*) $cm^{-1}$. UV $\lambda_{max.}^{MeOH}$: 243 mμ (c = 16,900).

| NMR ($CDCl_3$): | Protons assigned | at δ values |
|---|---|---|
| | $C_1$ | 7.00 (*d*, J=10 Hz) |
| | $C_2$ | 6.20 (*d,d*, J=10 and 2 Hz) |
| | $C_4$ | 6.05 (broad, *s*) |
| | $C_{18}$ | 4.38 (AB, *q*, J=10 Hz) |
| | $C_{21}$-methyl | 2.20 (*s*) |
| | $C_{19}$-methyl | 1.27 (*s*) |

Analysis: $C_{21}H_{27}N_1)_8$ Requires: C=67.54; H=7.29; N=3.75%; Found: C=67.66; H=7.56; N=3.70;

B. The 1 gram aliquot was taken up in methanol (30 mls), ammonium acetate (3.0 g) was added and the stirred solution cooled in an ice-bath. Zinc dust (3.0 g) was added and the stirring continued for 40 mins. The mixture was then diluted with ethyl acetate and water, filtered and the aqueous layer separated off. The organic extract was washed with water, dried ($Na_2SO_4$) and evaporated to dryness. Chromatography of the residue eluting with benzene containing 0% rising to 6% ethyl acetate and final purification by preparative t.l.c. (silica gel) afforded $\Delta^1$-18-hydroxy-progesterone (18-hydroxypregna-1,4-diene-3,20-dione) (220 mg., 23%) which was recrystallized from ethyl acetate/hexane. m.p. 170°–3°. IR $\nu_{max.}^{KBr}$: 3550 (broad, *m*), 1660(*s*), 1620(m), 1600(*w*) $cm^{-1}$. UV $\lambda_{max.}^{MeOH}$: 245 mμ (ε = 15,800). $[\alpha]_D^{24.5}$ = +75° (c = 1.14, $CH_2Cl_2$); +74° (c + 0.68, $CHCl_3$).

| NMR ($CDCl_3$): | Protons assigned | at δ values |
|---|---|---|
| | $C_1$ | 7.00 (*d*, J=10 Hz) |
| | $C_2$ | 6.17 (*d,d* J=10 and 2 Hz) |
| | $C_4$ | 6.03 (broad, *s*) |
| | $C_{18}$ | 3.73 (*s*) |
| | $C_{21}$-methyl | 1.50 (*s*) |
| | $C_{19}$-methyl | 1.18 (*s*) |

Analysis: $C_{21}H_{28}O_3$ Requires: C, =76.78; H, =8.59% Found: C, =76.46; H, =8.31.

Mass spectrum: very weak molecular ion at 328, base peak at (M-18) mμ.

EXAMPLE 15

3β-Acetoxy-7α-hydroxy-5α-lanostan-32-yl Nitrate

3β-Acetoxy-5α-lanostan-7α-yl nitrite* (3 g) in dry benzene (500 ml) was irradiated using a 125 W high-pressure mercury vapour lamp with a Pyrex filter whilst a slow stream of dry oxygen was bubbled through the stirred solution. After 7 h (t.l.c. control) the solvent was evaporated off, and the residue chromatographed on silica (50 g). Elution with benzene — light petroleum (b.p. 40°–60°) (60:40 v/v) afforded the above nitrate (1.4 g, 44%), m.p. (from ethanol) 146°–149° (dec.), $[\alpha]_D$ = 14° (c 0.14), $\nu_{max.}$ (Nujol) 3540 and 3480 (—OH), 1720 and 1265 (—OAc), and 1630, 1620 and 1280 (—$ONO_2$) $cm^{-1}$. τ 5.08 and 5.45 (2H, ABq, J 10Hz, C-32 $H_2$), ca. 5.5 (1H, c-3α H, obscured by C-32 $H_2$ signal), and 5.96 (1H, m, C-7β H) (Found: C, 70.05; H, 10.1; N, 2.5. $C_{32}H_{55}NO_6$ requires C, 69.9; H, 10.1; N, 2.55%).

*Batten et al. J. Chem. Soc. Perkin I, 1972, 739; Boar et al. ibid 1972, 749.

EXAMPLE 16

3β-Acetoxy-5α-lanost-7-en-32-yl Nitrate

The nitrate from Example 15 (1 g) in dry pyridine (30 ml) was treated with methane sulphonyl chloride (2 ml) at 0° for 24 h. The solution was poured into water and extracted with ether to give 3β-acetoxy-32-nitrato-5α-lanostan-7α-yl methanesulphonate, $\nu_{max.}$ (carbon tetrachloride) 1735 and 1240 (—OAc), 1633 and 1280 (—$ONO_2$), and 1345 and 1175 (—OMs) $cm^{-1}$. This material in benzene (100 ml) was stirred with Woelm basic alumina (20 g) for 12 h (t.l.c. control). The alumina was filtered off and washed thoroughly with ether. The combined filtrates were evaporated and the residue chromatographed on silica (50 g). Elution with benzene — light petroleum (b.p. 60°–80°) (40:60 v/v) afforded 3β-acetoxy-5α-lanost-7-en-32-yl nitrate (830 mg, 86%), m.p. (from benzene-ethanol) 90°–91°, $[\alpha]_D$+46.4° (c 0.12), $\nu_{max.}$ (carbon tetrachloride) 1735 and 1240 (—OAc), and 1635 and 1280 (—$ONO_2$) $cm^{-1}$, τ 4.65 (1H, m, C-7H), 5.12 and 5.76 (2H, ABq, J 12Hz, C-32 $H_2$), and 5.45 (1H, m, C-3α H) (Found: C, 72.5; H, 10.0; N, 2.55. $C_{32}H_{53}NO_5$ requires C, 72.3; H, 10.05; N, 2.6%).

EXAMPLE 17

5α-Lanost-7-ene-3β,32-diol 3-Acetate

3β-Acetoxy-5α-lanost-7-en-32-yl nitrate (300 mg) in glacial acetic acid (50 ml) was stirred at room temperature for 3.5 h with activated zinc dust (5 g). The mixture was filtered through Celite and the filter cake washed thoroughly with ether. The total filtrate was poured into water and extracted with ether. The extracts were washed with 1N sodium carbonate solution, then water, dried and evaporated. Crystallisation of the residue from methanol gave 5α-lanost-7-ene-3β,32-diol 3-acetate (230 mg, 84%), m.p. 152°–153°, $[\alpha]_D$ +32.5° (c 0.28), $\nu_{max.}$ (carbon tetrachloride) 3530 (—OH) and 1735 and 1240 (—OAc) $cm^{-1}$, τ 4.63 (1H, m, C-7H), 5.50 (1H, m, C-3α H), and 6.36 and 6.76 (2H, ABq, J 10Hz, C-32 $H_2$). (Found: C, 78.9; H, 11.0. $C_{32}H_{54}O_3$ requires C, 79.0; H, 11.2%).

EXAMPLE 18

3β-Acetoxy-5α-lanost-7-en-32-al

5α-Lanost-7-ene-3β,32-diol 3-acetate (100 mg) in acetone (40 ml) was cooled to −30° and Jones chromium trioxide reagent (3 drops) added. After 1 h the solution was allowed to warm to room temperature and after a further 5 min. the mixture was poured into water containing 10% methanol. Extraction with ether gave the above 32-aldehyde (90 mg, 90%), m.p. (from methanol) 130°–131°, $[\alpha]_D$ +27.5° (c 0.13) (lit.[1], m.p. 144°–145° (sealed tube), $[\alpha]_D$ +24°), $\nu_{max.}$ (Nujol) 1730 and 1250 (—OAc) and 1712 (—CHO) $cm^{-1}$, τ 0.38 (1H, *s*, —CHO), 4.6 (1H, m, C-7 H), and 5.5 (1H, m, C-3α H), identical with an authentic sample.

I claim:

1. A process for the preparation of a mononitrate ester of a diol whereby a nitrite ester of an alcohol having a hydrogen atom which is or is able to be conformationally adjacent to the hydroxy group and in which the atoms joining the hydrogen atom and the hydroxyl group include at least two adjacent atoms forming part of a ring, is photolysed in the presence of molecular oxygen, whereby a corresponding compound is formed in which the said hydrogen atom is replaced by a nitrooxy group.

2. A process according to claim 1 in which the photolysis is effected in a solvent selected from aromatic compounds, halogenated aromatic compounds, halogenated hydrocarbons, halogenated ethers and nitriles.

3. A process according to claim 2, in which the solvent is selected from benzene, toluene, xylene, hexafluorobenzene, chlorobenzene, the chlorotoluenes, the chloroxylenes, chloroalkanes, chlorofluoroalkanes, perfluoroalkanes, perfluoroalkylamines, perfluoromethyltetrahydrofuran and acetonitrile.

4. A process according to claim 2 in which a single phase mixture or an emulsion of two solvents is used.

5. A process according to claim 1 in which the reaction is effected at a temperature of from 40° to the freezing point of the reaction mixture.

6. A process according to claim 1 in which the reaction is effected using light of a wavelength of 300 nm or more.

7. A process according to claim 6 in which the wavelength is 300 – 380 nm.

8. A process according to claim 1 in which the starting nitrite is a steroid.

9. A process according to claim 8 in which the steroid is a nitrite ester of a 6-hydroxy-, 11-hydroxy-, 7α-hydroxy- or 20-hydroxy-steroid.

10. A process according to claim 8 in which the steroid contains substituents and double bonds selected from a keto, hydroxy or acyloxy group in the 3-position; alkyl groups in any of the 2-, 4-, 6-, 10-, 13-, 14- and 16-positions; a keto, ketal or orthoester group at the 20-position; a keto group or hydroxy and/or hydrocarbon or acyl groups at the 17-position; a hydroxy or keto group at the 11- or 12-position, a hydroxy group at the 6-, 7- or 20-position, an esterified hydroxy group at the 21-position, a double bond at 5-position or the 1- and/or 4-position and a halogen atom in the 11- or 6-position.

11. A process according to claim 8 in which the steroid is in the pregnane, lanostane, norpregnane, oestrane or cholestane series.

12. A process according to claim 1 in which the nitrate obtained is reductively cleaved to yield the corresponding alcohol.

13. A process according to claim 12 in which the reaction is effected using a source of nascent hydrogen.

14. A process according to claim 12 in which the diol mononitrate produced is subjected to further reactions selected from oxidation, dehydration, isomerisation, esterification, etherification and hydrolysis, before the nitrate group is cleaved.

15. A process according to claim 1 in which a radiolabelled hydroxy group is introduced.

* * * * *